(12) United States Patent  
Armand et al.

(10) Patent No.: US 12,239,406 B2  
(45) Date of Patent: Mar. 4, 2025

(54) SURGICAL ROBOTIC SYSTEM

(71) Applicant: ECENTIAL ROBOTICS, Gieres (FR)

(72) Inventors: David Armand, Saint Egreve (FR); Stéphane Lavallee, St Martin d'Uriage (FR)

(73) Assignee: ECENTIAL ROBOTICS, Gieres (FR)

( * ) Notice: Subject to any disclaimer, the term of this patent is extended or adjusted under 35 U.S.C. 154(b) by 183 days.

(21) Appl. No.: 17/770,657

(22) PCT Filed: Nov. 12, 2020

(86) PCT No.: PCT/EP2020/081903  
§ 371 (c)(1),  
(2) Date: Apr. 21, 2022

(87) PCT Pub. No.: WO2021/094448  
PCT Pub. Date: May 20, 2021

(65) Prior Publication Data  
US 2022/0361972 A1 Nov. 17, 2022

(30) Foreign Application Priority Data

Nov. 12, 2019 (EP) ..................................... 19306463

(51) Int. Cl.  
*A61B 34/37* (2016.01)  
*A61B 34/00* (2016.01)  
(Continued)

(52) U.S. Cl.  
CPC .............. *A61B 34/37* (2016.02); *A61B 34/25* (2016.02); *B25J 9/1674* (2013.01);  
(Continued)

(58) Field of Classification Search  
CPC ... A61B 34/37; A61B 34/25; A61B 2034/303; A61B 90/39; A61B 34/20; A61B 34/30;  
(Continued)

(56) References Cited

U.S. PATENT DOCUMENTS

2006/0142657 A1 6/2006 Quaid et al.  
2011/0082365 A1* 4/2011 McGrogan ......... A61B 17/3421  
600/424  
(Continued)

FOREIGN PATENT DOCUMENTS

EP 2868277 A1 5/2015  
EP 3361977 A1 8/2018  
(Continued)

OTHER PUBLICATIONS

Extended European Search Report in related EP application No. EP19306463, mailed Apr. 15, 2020.  
(Continued)

*Primary Examiner* — Wade Miles  
*Assistant Examiner* — Mohammed Yousef Abuelhawa  
(74) *Attorney, Agent, or Firm* — Thomas | Horstemeyer, LLP

(57) ABSTRACT

Disclosed is a surgical robotic system comprising a robotic arm holding an end-effector and a control unit for controllably moving the robotic arm and maintaining the end-effector in at least one target position relative to a patient. The control unit can, based on a first input continuously applied onto the robotic arm, activate a hand guiding mode wherein the robotic arm is freely movable by the user; based on a second input different from the first input, continuously applied onto the robotic arm, activate a computed trajectory mode wherein the robotic arm moves to a target position according to a computed trajectory; when the computed trajectory is activated, detect that the end-effector meets a predetermined safety condition and automatically switch to a servo-controlled mode wherein the robotic arm is automatically movable to maintain the end-effector in the target position relative to a tracker attached to the patient.

16 Claims, 5 Drawing Sheets

(51) Int. Cl.
*A61B 34/20* (2016.01)
*A61B 34/30* (2016.01)
*B25J 9/16* (2006.01)

(52) U.S. Cl.
CPC . *A61B 2034/2046* (2016.02); *A61B 2034/303* (2016.02); *A61B 2034/305* (2016.02)

(58) Field of Classification Search
CPC ........... A61B 2090/3937; B25J 9/1674; G05B 2219/45171
See application file for complete search history.

(56) References Cited

U.S. PATENT DOCUMENTS

| | | | |
|---|---|---|---|
| 2011/0190790 A1 | 8/2011 | Summerer et al. | |
| 2012/0190981 A1* | 7/2012 | Harris | A61B 5/14 604/95.01 |
| 2014/0222207 A1* | 8/2014 | Bowling | A61B 34/30 700/261 |
| 2014/0350571 A1 | 11/2014 | Maillet et al. | |
| 2016/0166333 A1* | 6/2016 | Wang | A61B 34/10 600/476 |
| 2019/0090966 A1* | 3/2019 | Kang | A61B 17/1671 |
| 2020/0138530 A1* | 5/2020 | Nowatschin | B25J 19/0004 |

FOREIGN PATENT DOCUMENTS

| | | |
|---|---|---|
| JP | 2008-538184 A | 10/2008 |
| WO | 2006/091494 A1 | 8/2006 |
| WO | 2013101753 A1 | 7/2013 |
| WO | 2016187290 A1 | 11/2016 |
| WO | 2019023386 A2 | 1/2019 |
| WO | 2019023386 A3 | 1/2019 |

OTHER PUBLICATIONS

PCT International Search Report in related PCT Application No. PCT/EP2020/081903, mailed Feb. 11, 2021.

* cited by examiner

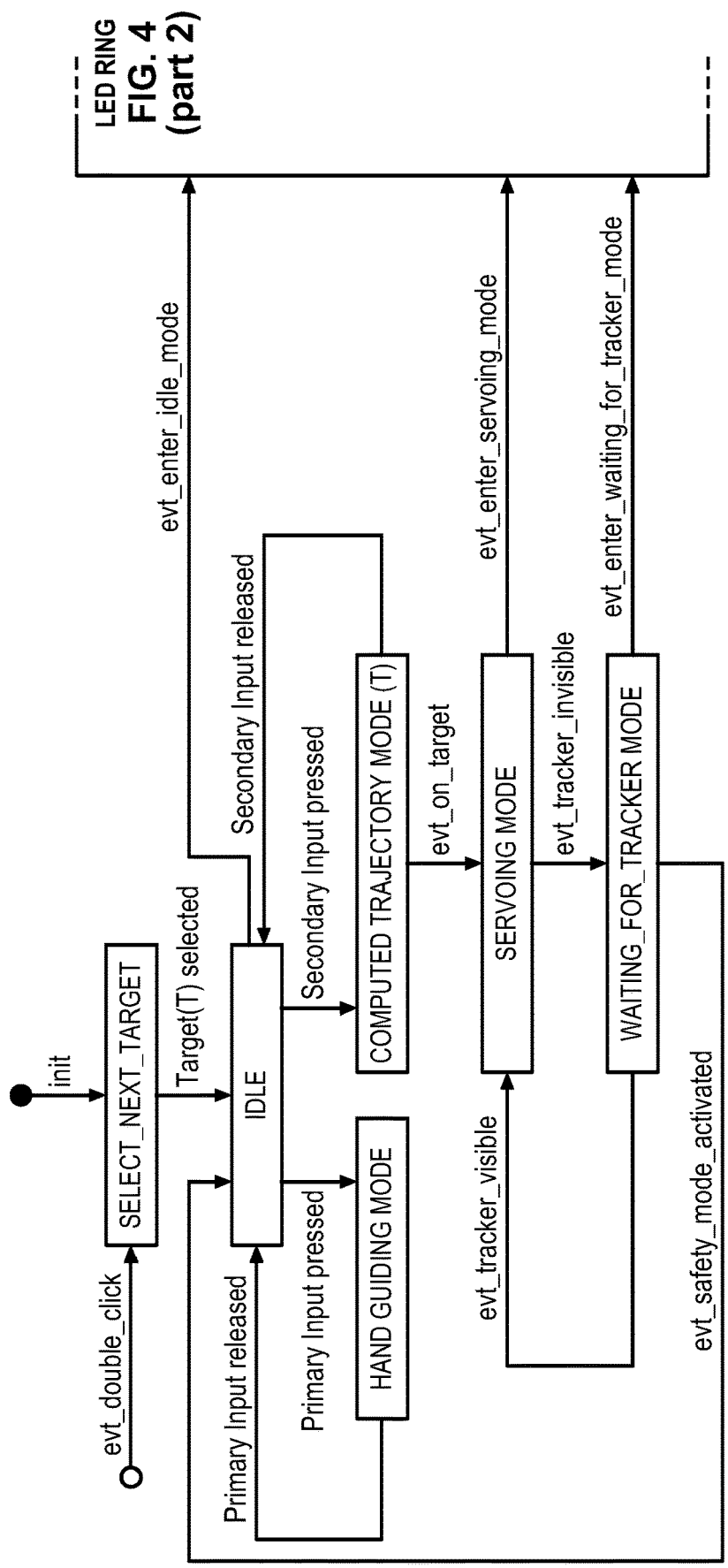

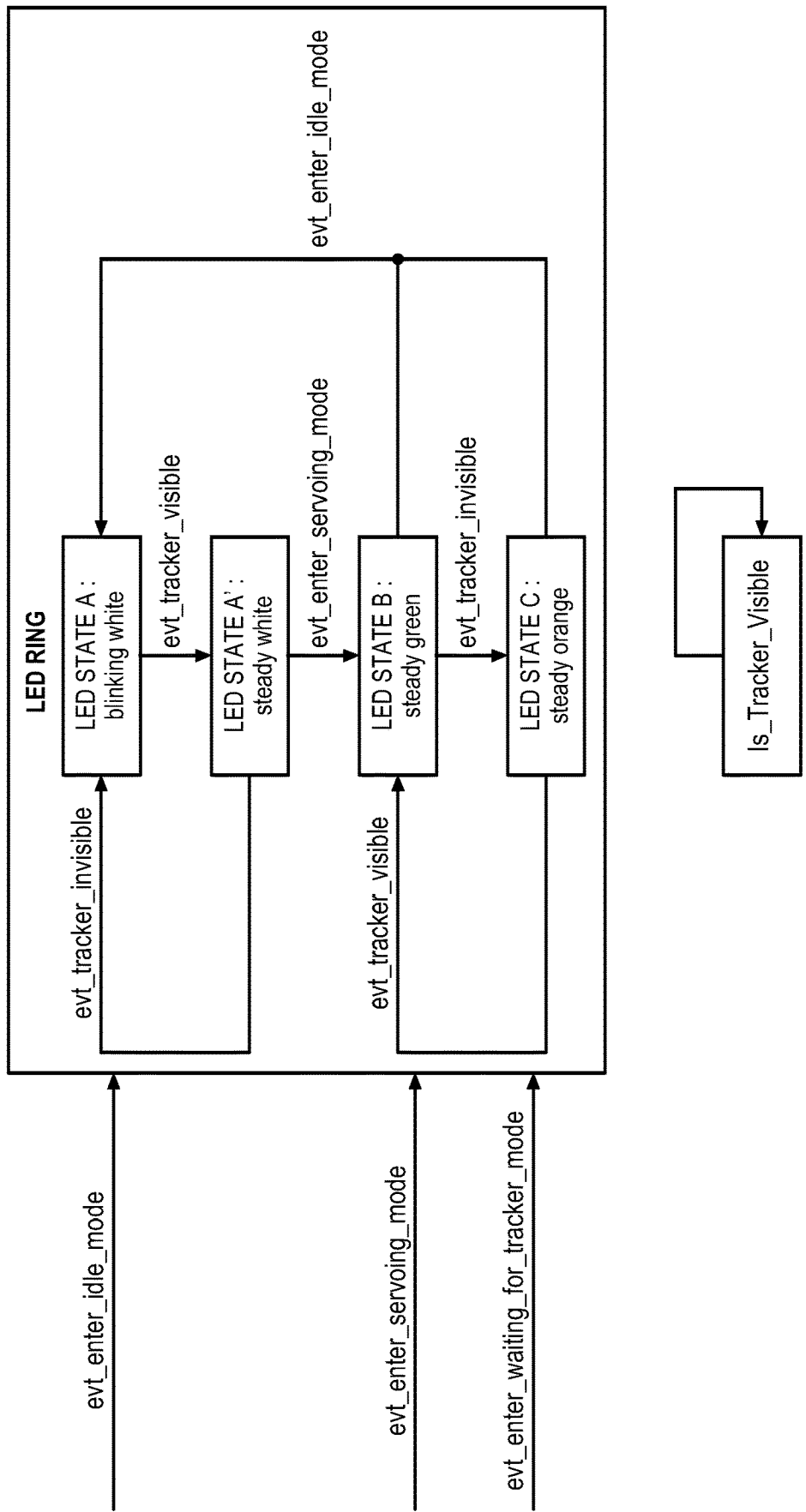
FIG. 4 (part 2)

SURGICAL ROBOTIC SYSTEM

CROSS REFERENCE TO RELATED APPLICATIONS

This application is the 35 U.S.C. § 371 national stage application of PCT Application No. PCT/EP2020/081903, filed Nov. 12, 2020, which application claims the benefit of European Application No. EP 19306463.1 filed Nov. 1, 2019, both of which are hereby incorporated by reference herein in their entireties.

FIELD OF THE INVENTION

The present invention relates to a surgical robotic system comprising a robotic arm holding an end-effector and a control unit configured to controllably move the robotic arm and maintain the end-effector in at least one target position relative to a patient.

BACKGROUND OF THE INVENTION

Surgical robotic arms are already used for assisting a user (e.g. a surgeon) during a surgical intervention.

For example, in spine surgery, the user may have to implant one or several screws into at least one vertebra. The robotic arm may assist the user by holding a drill guide and maintaining the drill guide according to a planned axis. The user may thus use a handheld drill passing through the drill guide held by the robotic arm to drill a hole intended to receive the screw in a vertebra along the planned axis.

However, when using such robotic arms, several challenges are to be met.

A first challenge relates to safety, i.e. ensuring that the robotic arm cannot do anything harmful for the patient and the medical staff.

A second challenge is to define a suitable collaboration between the user and the robotic arm. By "collaboration" is meant that the robotic arm does not replace the human user but assists him/her by complementing his/her capabilities and allowing him/her to concentrate on specific tasks.

Known robotic arms exist which move toward a target position as long as a continuous pressure is exerted by a user onto a button or a pedal. However, such displacement is slow and thus has the effect of significantly increasing operative time. In addition, the robotic arm trajectory may not take into account all obstacles present in the vicinity of the patient. For safety reasons, the robotic arm stops as soon as the user releases the button or pedal.

On the other hand, since the patient may move during the surgical intervention, e.g. due to breathing or to a mechanical reaction to the use of a surgical tool to treat the patient, it would be desirable that the robotic arm be able to maintain the end-effector in the target position relative to the patient.

Document US 2011/0190790 teaches a robotic system comprising a robotic arm holding an end-effector and a control unit. Virtual walls define a safe work region for the robotic arm. The control unit is configured to stop the robotic arm or to provide a haptic feedback when the robotic arm exits from the working zone.

Document US 2014/0350571 teaches a robotic system comprising a first robotic arm holding an end-effector, a second robotic arm holding sensors in contact with the patient's body and a control unit configured to adjust the position of the first arm based on displacements of the patient's body detected by the second arm.

SUMMARY OF THE INVENTION

A goal of the invention is to design a surgical robotic system which allows improving collaboration between the user and the robotic arm while ensuring safety.

To that end, the invention provides a surgical robotic system comprising a robotic arm holding an end-effector and a control unit configured to controllably move the robotic arm and maintain the end-effector in at least one target position relative to a patient, wherein the control unit is configured to:
(i) based on a first input continuously applied by a user onto the robotic arm, activate a hand guiding mode wherein the robotic arm is freely movable by the user;
(ii) based on a second input different from the first input, continuously applied by the user onto the robotic arm, activate a computed trajectory mode wherein the robotic arm moves to a target position according to a computed trajectory;
(iii) when the computed trajectory mode is activated, detect that the end-effector meets at least one predetermined safety condition and automatically switch to a servo-controlled mode wherein the robotic arm is automatically movable to maintain the end-effector in the target position relative to a tracker attached to the patient.

Said robotic system thus combines at least three modes of use: hand guiding mode, computed trajectory mode and servo-controlled mode, said combination of modes allowing optimizing the collaboration between the robotic arm and the user. In the hand guiding mode, the user is allowed to move the robotic arm freely and quickly to bring the end-effector in a rough position close to the target position; in the computed trajectory mode, the robotic arm moves the end-effector in the precise target position, while still being controlled by the user thanks to the second input; in the servo-controlled mode, the robotic arm moves autonomously to maintain the end-effector in the target position, if safety conditions are met. Thus, throughout operation of the robotic arm, safety is ensured by the user and/or the control unit.

In some embodiments, the predetermined safety condition is that the tracker attached to the patient remains in a controlled volume relative to a base of the robotic arm, a dimension of said controlled volume being greater in a direction of an expected motion of the tracker than in a direction of an unexpected motion of said tracker.

In some embodiments, the target position is selected among:
a drilling axis;
a drilling axis and a drilling depth;
a cutting plane;
an optimal working position of an active surgical tool.

In some embodiments, the control unit is configured to adjust the computed trajectory based on an orientation of the robotic arm imposed by the user in the hand guiding mode.

In some embodiments, the system comprises a user interface coupled to the control unit and configured to provide information on the current mode.

Said user interface may comprise a display monitor arranged on the robotic arm and configured to display a changing graphical item depending on the current mode.

Said user interface may comprise a ring including a plurality of LEDs configured to have predetermined colors and/or blinking conditions depending on the current mode.

In some embodiments, the control unit is further configured to activate a safety mode inhibiting movement of the robotic arm, based on a detection of motion of the robotic arm exceeding a predetermined amplitude, direction, acceleration and/or speed in the servo-controlled mode.

In some embodiments, the control unit is configured to successively maintain the end-effector in a plurality of target positions.

In some embodiments, the robotic arm comprises a first switch configured for application of the first input by the user and a second switch distinct from the first switch configured for application of the second input by the user.

The control unit may be configured to enable a transition between two successive targets when a double-click of the second switch is done by the user at any time during the surgical procedure.

In some embodiments, the control unit is configured to put the robotic arm in idle mode when the tracking of said robotic arm is not enabled and the surgical robotic system is either in hand guiding mode or computed trajectory mode.

In some embodiments, the control unit is configured to put the robotic arm in a specific waiting mode when the tracking of said robotic arm is lost when the surgical robotic system is in the servo-controlled mode, wherein said specific waiting mode can switch back to the servo-controlled mode when the tracking is retrieved.

Another object is a process for positioning an end-effector held by a robotic arm relative to a patient, comprising:
 (i) based on a first input continuously applied by a user onto the robotic arm, activating a hand guiding mode wherein the robotic arm is freely movable by the user;
 (ii) based on a second input different from the first input, continuously applied by the user onto the robotic arm, activating a computed trajectory mode wherein the robotic arm moves to a target position according to a computed trajectory;
 (iii) when the computed trajectory is activated, detect that the end-effector is within a controlled volume around the target position, and automatically switch to a servo-controlled mode wherein the robotic arm is automatically movable within said controlled volume to maintain the end-effector in the target position relative to the patient.

In some applications, the target position is planned relative to the patient's spine.

In some applications, the target position is planned relative to a patient's bone.

BRIEF DESCRIPTION OF THE FIGURES

Further features and advantages of the invention will appear from the detailed description that follows, based on appended drawings wherein:

FIG. 4 is a state machine showing the operation of the robotic system in its different modes.

DETAILED DESCRIPTION OF EMBODIMENTS OF THE INVENTION

Figure 1:
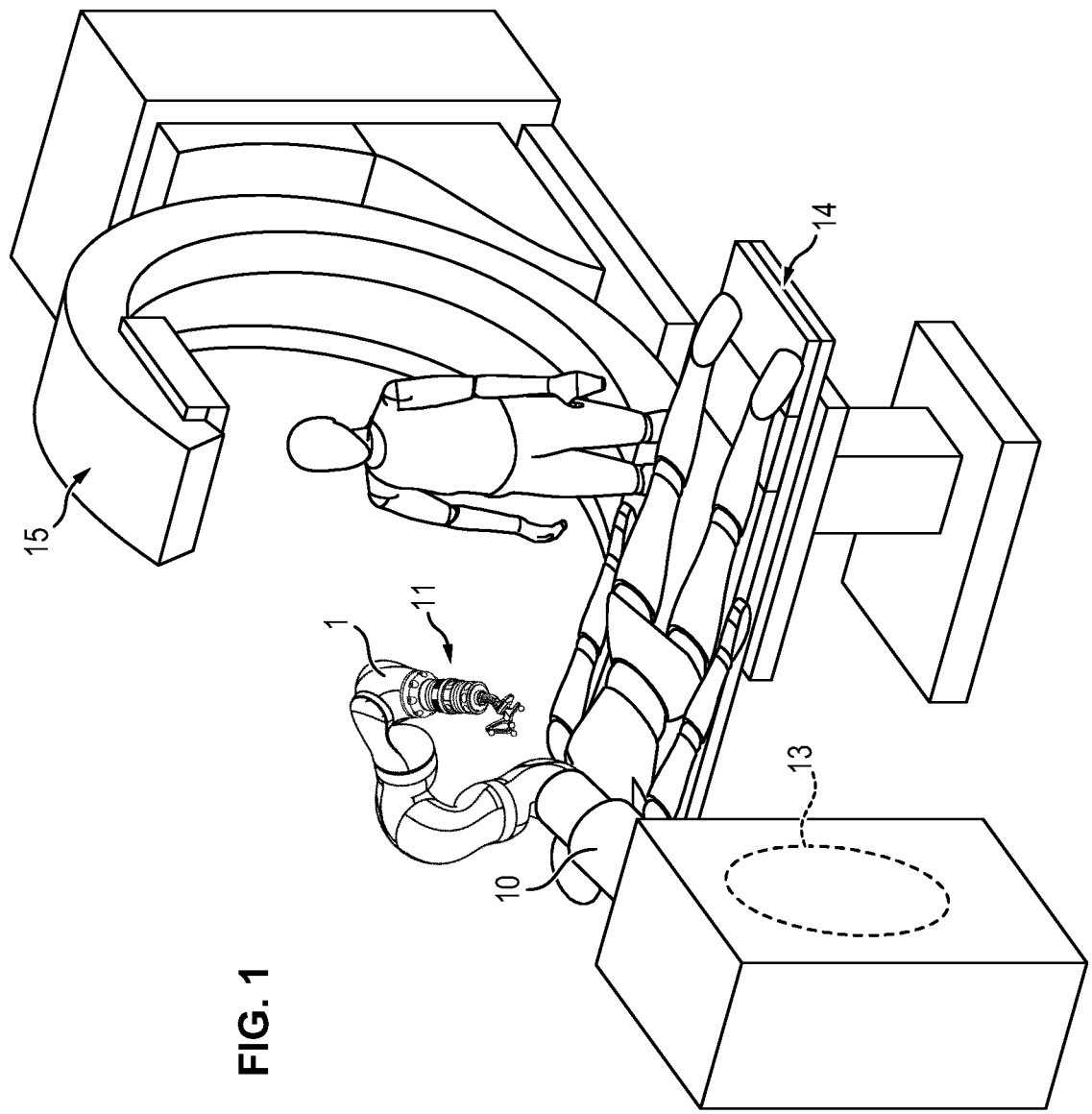
FIG. 1 illustrates a general overview of the robotic system.

The invention can be implemented in the context of a surgical intervention carried out onto a patient's bone, including but not limited to: implantation of orthopedic implants such as pedicular screws in the spine, implantation of various orthopedic implants in bones, reduction and fixation of fractures during traumatological procedures, or just positioning guides or canulae at a desired position with respect to a predefined target.

More particularly, the invention can be used for maintaining targets for pedicle screw placement defined in a preoperative or intraoperative image-based planning step.

In this regard, the robotic system can be coupled to other surgical systems: imaging devices such as a motorized C-arm imaging unit (as described in EP2868277) or a CT scan unit such as a Mobius Airo.

These systems offer 2D and 3D imaging capabilities, and navigation capabilities when coupled to a localization system, such as described in EP3361977.

In view of carrying out said navigation, the end-effector and/or the tool(s) used during the surgical intervention are equipped with a tracker, e.g. an optical, electromagnetic, ultrasonic, or inertial tracker and measured by at least one localization system. Another tracker is mounted onto the patient bone to be operated (or onto another bone that can assumed fixed to the operated bone) and is also detected by the localization system, it is designated as a reference tracker attached to the patient The robotic system comprises:
 a robotic arm having a proximal end extending from a base, which may be a movable cart or an imaging device, or may be attached to the operating table,
 an end-effector attached at a distal end of the robotic arm, and
 a control unit configured to controllably move the robotic arm and maintain the end-effector in at least one target position relative to a patient.

The robotic arm comprises a plurality of degrees of freedom in translation and/or rotation. Usually, the robotic arm comprises six or seven motorized degrees of freedom. To that end, the robotic arm comprises a plurality of articulated segments driven by motors. A robotic arm can be for example the LBR Med™ robot provided by KUKA.

The end-effector comprises a hand grip configured to be held by a user's hand for manipulating the robotic arm, notably in the hand guiding mode that will be described below.

In some embodiments, the hand grip comprises a first and a second switches configured to be separately actuated by the user to trigger the operating modes of the robotic arm. Said switches may comprise push-buttons, resistive switches, piezoelectric switches, etc. Although said switches may be arranged in another part of the robotic arm, they are preferably arranged on the hand grip so that the user may use a single hand to actuate one of said switches and at the same time handle the end-effector either to move the robotic arm (in the hand guiding mode) or to follow the movement of the robotic arm (in the computed trajectory mode).

In some embodiments, the hand grip comprises at least one user interface configured to provide information about the current mode. Although said user interface may be arranged in another part of the robotic system, it is advantageously located on the hand grip or on its vicinity so as to allow the user to concentrate on the end-effector when the robotic arm is operated. According to an embodiment, the user interface comprises a display with a changing graphical item (e.g. text, marks with variable color, etc.) depending on the current mode. According to another embodiment, the user interface may comprise a plurality of LEDs. The LEDs may be configured to have predetermined colors and/or blinking conditions depending on the current mode. Said LEDs ring may be arranged as a ring around the hand grip or around the robotic arm in the vicinity of the hand grip.

The end-effector also comprises a passive or active tool holder. A passive tool holder is configured to hold a guide in which slides a surgical tool, which may be a drill guide, a drill, a cutting guide, or any active tool. An active tool holder is configured to hold an active surgical tool, which may be a drill, an ultrasonic cutter, a burr, or any active tool. The active tool holder may also hold an actuator comprising several motorized degrees of freedom that than move and activate an active surgical tool. In a preferred embodiment, the tool holder holds a linear actuator that can translate a drill or burr along its axis. The tool holder also comprises a tracker detectable by the localization system.

The hand grip and/or the tool holder can be reusable and sterilizable or can be used as disposable components.

The control unit comprises a processor, a data storage device and a communication device. The control unit may advantageously be embedded in the base of the robotic arm. The base of the robotic arm also comprises switches, such as a power switch, an emergency button and the like.

The robotic system may be operated as follows.

Intraoperative 3D and/or 2D images are acquired with an imaging system such as a C-arm.

Planning may be done by the surgeon on these images, by defining at least one surgical target for the robotic system to process. These targets are defined in the coordinate system of the imaging system.

The robotic system, which may be mobile on the wheels of the cart forming the base of the robotic arm, is brought near the surgical table.

The patient is equipped with at least one reference tracker detectable by the localization system. Another tracker is also attached to the end-effector, in particular to the tool holder. Based on localization data of both trackers, the control unit is capable of determining a relative position of the end-effector relative to the patient. Various registration methods can be used to determine a transform between the coordinate system of the patient reference tracker and the imaging system. Therefore, the targets are known in a coordinate system attached to the patient reference tracker. Since the robot is equipped with a tracker, it is possible to compute the transform between the current end-effector position and the target position, and to assign the robot to a position aligned with the target.

As an alternative to the planning based on the images, it may also be possible to define targets directly in the coordinate system of the reference tracker attached to the patient. For example, a navigation pointer may be used to define a target, it is then removed and the robot end-effector axis is aligned to this target position.

The robotic system start-up procedure is launched, including security tests.

When ready, the robotic arm is in an idle mode. In this idle mode, the robotic arm cannot move by itself.

The user can then activate the first switch in a continuous manner to enable a hand guiding mode wherein the user can freely move the robotic arm by manipulating the hand grip. This mode can be implemented using conventional collaborative modes of robotic devices such as the KUKA LBR iiwa™ robotic arm. The user may thus bring easily the end-effector close to the first surgical target defined in the planning. Since the robotic arm is continuously handled and controlled by the user, its displacement may be relatively quick while allowing avoiding obstacles. The hand guiding mode is maintained as long as the activation of the first switch is maintained. As soon as the user stops activating the first switch, the control unit stops the motors so that the user can no longer move the robotic arm, and the robotic arm cannot move by itself (idle mode). In a preferred embodiment, the first switch is located on the end-effector but proximally, close to the robot base.

Once the tracker installed on the tool holder of the end-effector on the robotic arm enters the field of measurements of the localization system and is accurately located by the localization system, the operator can stop the hand guiding mode and enable a computed trajectory mode, by continuously activating the second switch instead of the first switch. The possible transition between the hand guiding mode and the computed trajectory mode may be visualized via the user interface, e.g. by changing LED colors and/or blinking conditions when the tracker becomes detectable by the localization system. In a preferred embodiment, the second switch is located on the end-effector but distally, close to the extremity opposite to the base.

In this computed trajectory mode, the user only accompanies the robotic arm, said arm moving autonomously according to a trajectory computed previously to the surgical target. The safety is ensured by the obligation of continuous activation of the second switch by the user. As soon as the user stops activating the second switch, the control unit stops the motors so that the robotic arm can no longer move. The computed trajectory mode may thus be considered as a collaborative mode of the robotic system. When the robot has reached the target position, the user interface indicates a signal. In a preferred embodiment, the LEDs become green and it means the user has the green light to perform surgery and insert instruments through the tool holder.

In case the end-effector tracker is no longer detectable by the localization unit, e.g. because the tracker is hidden by another item in the optical localization system field of view in case of optical localization, the control unit exits from the current mode and stops the robotic arm. Said situation may be indicated by the user interface, e.g. with a specific LED color and/or blinking condition. In a preferred embodiment, the LEDs become blinking white if the current mode was the hand guiding mode or the computed trajectory mode or blinking orange if the current mode was the servo-controlled mode.

Once the target has been reached and the user interface gives the green light, in case the user exerts excessive forces on the robot end-effector and the end-effector tracker is no longer aligned with the target within a given range, the control unit first tries to bring the robot back to its target and the user interface displays an orange light for example, but if the robot is not successful, the control unit exits from the servo-controlled mode and stops the robotic arm. Said situation may be indicated by the user interface, e.g. with a specific LED color and/or blinking condition. In a preferred embodiment, the LEDs become orange.

In a preferred embodiment, the user may impose a specific orientation of the tool holder during the hand guiding mode, and this global orientation or the tool holder is then preserved in its essential components to reach the target. This orientation may be in particular decided to pre-position the robotic arm in a position favorable for the surgical treatment, in order to avoid collisions with other surgical instruments for example. If the user sees that a collision may occur when the user presses the second switch, the user may stop, come back to the hand guiding mode using the first switch, and change the orientation of the tool holder in this mode, and then move forward to the target by pressing the second switch. In this mode, the final target calculation is performed to orientate the robot arm as close as possible as the initial robot arm position. This mode benefits from the redundancy of a six-axis or seven-axis robot to align a linear trajectory to a final target position which requires only five degrees of freedom. Among an infinite set of orientations that can be used for the robot around the tool holder axis, the one closest to the initial robot position is selected.

In the next section, the description is focused on the case of a passive tool holder in which slides the various surgical tools (drill, screwdriver, etc.).

Once the robotic arm has reached the planned surgical target, the user can release the second switch. Said situation may be detected based on a comparison between the position of the tracker of the end-effector and the desired target position. As none of the first and second switches is activated, the control unit triggers an autonomous mode, servo-controlled to the small movements of the patient (breathing for example) by a monitoring of the relative positions of the end-effector and the patient allowed by the tracking system. The transition between the computed trajectory mode and the servo-controlled mode may be visualized via the user interface, e.g. by different LED colors and/or different blinking conditions.

In this servo-controlled mode, the user can rely on the assistance provided by the robotic system, which holds a guide or the tool itself, to perform the planned operation. The user then does not need to activate a switch and may concentrate on the tool used to perform the intervention.

In the case of a pedicular screw placement, the surgeon can manipulate a drill. The drilling can be achieved by a manual drill bit or an ultrasonic tool and the like that is sliding into the tool holder.

In another embodiment, the drill instrument can be an active end-effector, such as a small compact active robot for burring a bone.

For safety reasons, in the servo-controlled mode, the end-effector can only move and be servoed to the target if certain safety conditions are met. Several safety conditions can be implemented to authorize the servo-controlled mode to be activated, including one or several conditions in the following list:

(a) In a first embodiment, a safety condition is met if the end-effector position remains within a limited volume around the target position. For example, if the target moves by more than five millimeters in the coordinate system of the robotic arm base compared to its initial position, the safety condition will not be met and the robotic arm will stop, the user interface will display a signal, and the user will need to press again one of the switches to reactivate the robotic arm in either hand guiding or computed trajectory mode. Advantageously, said volume is updated in real time based on motions of the patient, such as breathing or mechanical reactions to the use of a tool on the patient.

(b) In another preferred embodiment, which is a more advanced feature, the safety condition is met if the detected motion of the reference bone tracker with respect to the robot base corresponds to an expected motion of the bone within a given range of eight millimeters for example, but the safety condition is not met if the detected motion exceeds three millimeters in the direction of unexpected motions. An expected motion can be the result of breathing modeling or a modeled interaction of the surgical tool with the bone that exerts a pressure onto the bone. Otherwise said, the safety condition corresponds to a volume in which the bone tracker may move, the volume having a dimension greater in a first direction which is a direction of an expected motion of the bone tracker than in a second direction which is a direction of an unexpected motion of the bone tracker.

(c) In another preferred embodiment, the safety condition is unmet if the detected motion of the reference bone tracker with respect the robot base has a speed exceeding a given threshold.

(d) In another preferred embodiment, the safety condition is unmet if the detected motion of the reference bone tracker with respect to the robotic arm base has an acceleration exceeding a given threshold. Such a situation may occur for example if the tracker attached to the patient using a magnetic fixation is inadvertently displaced during the surgical intervention. Indeed, a shock may cause the patient tracker to fall or to be displaced and, since the robotic arm is servoed to the position of the patient tracker, the robotic arm may move quickly and with a large amplitude to follow the falling or displaced tracker, which may hurt the patient and/or the medical staff.

The various safety conditions can be used individually or partly together.

The safety conditions described above do not substitute to standard safety conditions of surgical robotics, they are cumulated. For example, any deviation of the robotic arm position with respect to its target calculated in the bone reference tracker that exceeds a threshold of one millimeter triggers an alarm and a stop of the robot. Similarly, standard safety conditions that measure the consistency of redundant measurements of robot position sensors, robot force sensors, or simply excessive forces applied to the robot, trigger alarms and safety stops that remain valid.

The control unit may exit from the safety mode if the user activates either the first or the second switch.

The servo-controlled mode may be stopped by the user as soon as the operating step in the target position has been performed.

For example, if the user has drilled a hole in a vertebra according to a first target, the user may wish to move the robotic arm to the next target to drill a hole in another vertebra. In a preferred embodiment, if the user presses twice the second switch, with a double click, at any moment, the robotic arm will switch to the next planned target if there is one In some circumstances, the user may wish to remove the robotic arm from the operative site. For example, if the user has drilled a hole in a vertebra, he may wish to immediately place a pedicular screw in this hole. To that end, the user may continuously activate the first switch to trigger the hand guiding mode, and quickly displace the robotic arm away from the operative site in order to have enough room to perform the implantation of the pedicular screw. Then the user can activate continuously the second switch to bring the robotic arm back to its target position and perform more actions using the robot guidance in the servo-controlled mode.

After that, if a new screw is to be implanted, the user may select the next target with a double click such as described in a previous embodiment and perform the same sequence as described above, beginning with the hand guiding mode to quickly move the end-effector in the vicinity of the next target.

In a preferred embodiment, the holding tool is active and holding a drill for example. Once the end-effector has reached its target, the control unit moves the high-speed rotating drill along its axis in a linear motion, along a planned trajectory. The safety condition is met as long as the trajectory respects safety constraints. It represents an extension of the case described above wherein the position must respect safety constraints. For example, the active tool trajectory respects the safety conditions if the tool itself remains aligned with the target line calculated in the robot basis coordinate system.

FIG. 1 illustrates an embodiment of a surgical robotic system as described above in an operating room, in a context of spine surgery.

The operating room comprises an operating table 14. For spine surgery, the patient may be in prone position on the operating table, but for other surgical interventions the patient may be placed in another position. Although not shown, at least one tracker is rigidly attached to the patient, in particular to a vertebra in the case of spine surgery. Several reference trackers can be used, one per operated vertebra.

The operating table may also comprise an imaging system, such as a C-arm 15. The imaging system allows acquiring intraoperative images of the patient.

The robotic system comprises a robotic arm 1 comprising a base 10 and an end-effector 11, which will be described in greater detail with reference to FIGS. 2 and 3. The base is fixed to a mobile cart, which is immobilized relative to the operating table during the surgical intervention.

The control unit which controls the robotic arm may be embedded in the cart and is designated by reference 13.

Figure 2:
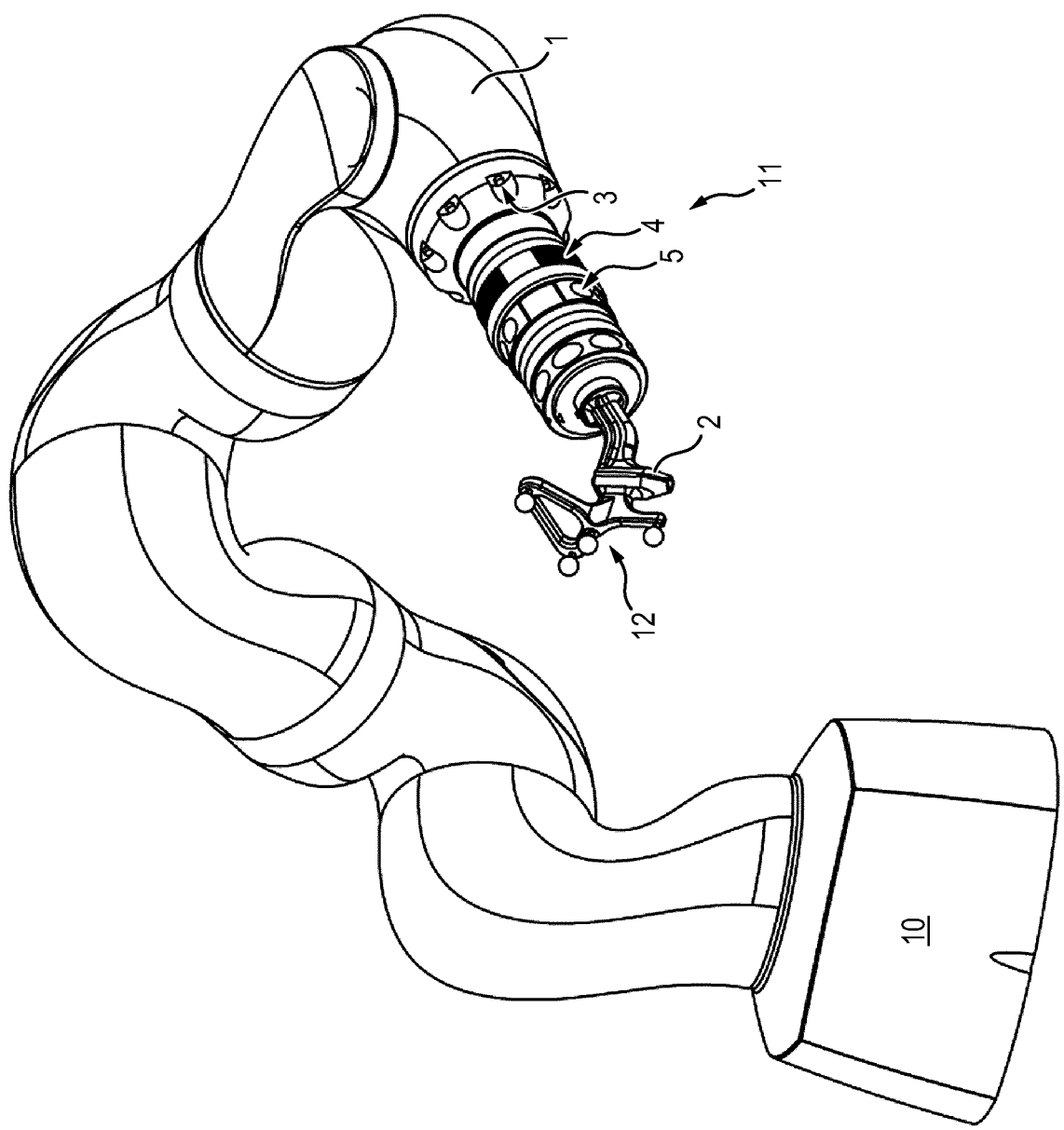
FIG. 2 is a perspective view of an embodiment of the robotic arm.

An enlarged view of the robotic arm is shown in FIG. 2.

The robotic arm 1 comprises a plurality of articulated segments. The terminal segment, opposite to the base 10, comprises an end-effector 11.

The end-effector 11 comprises a hand grip configured to be held by a user's hand. To that end, the hand grip may have an ergonomic shape, such as a cylindrical shape with a diameter adapted so that the hand grip may be at least partially surrounded by the user's hand.

The hand grip comprises two switches 4, 5 that are distinct from each other. The first switch is configured to trigger the hand guiding mode, whereas the second switch is configured to trigger the computed trajectory mode. To implement each of said modes, the user has to continuously activate the respective switch. In case the user releases the first or second switch while the robotic arm has not attained the target, the robotic arm stops immediately. The switches are advantageously arranged on the outer surface of the hand grip so that the user may handle the end-effector and activate a switch with a single hand.

The end-effector further comprises a LEDs ring 3 comprising a plurality of LEDs configured to emit light with different colors and/or different blinking conditions. For example, the LEDs may emit the following light signals:
 blinking white when the robotic arm is in the idle mode;
 steady white when the robotic arm is in either hand guiding mode or computed trajectory mode and the tracker is detectable by the localization system;
 steady green when the robotic arm is in the servo-controlled mode and the target is reached;
 steady orange when the tracker stops being detectable by the localization system in the servo-controlled mode.

Such a LED ring is convenient in that it may be seen by the user whatever the orientation of the end-effector; however, the user interface may take any other form. It can be for example a small display of one or two inches in diagonal that can rotated anywhere around the robot end-effector.

The end-effector holds a tool holder 2, which may be for example a linear and cylindrical guide for an active tool handheld by the user, such as a drill. The guide allows maintaining the active tool according to a determined orientation and at a determined distance of the patient.

A tracker 12 is attached to the end-effector and is used to determine the position and orientation of the end-effector relative to the tracker attached to the patient. A high speed three-dimensional camera is used to obtain such measurements, with low latency less than ten milliseconds, and framerate in the range of one hundred or more hertz.

Figure 3:
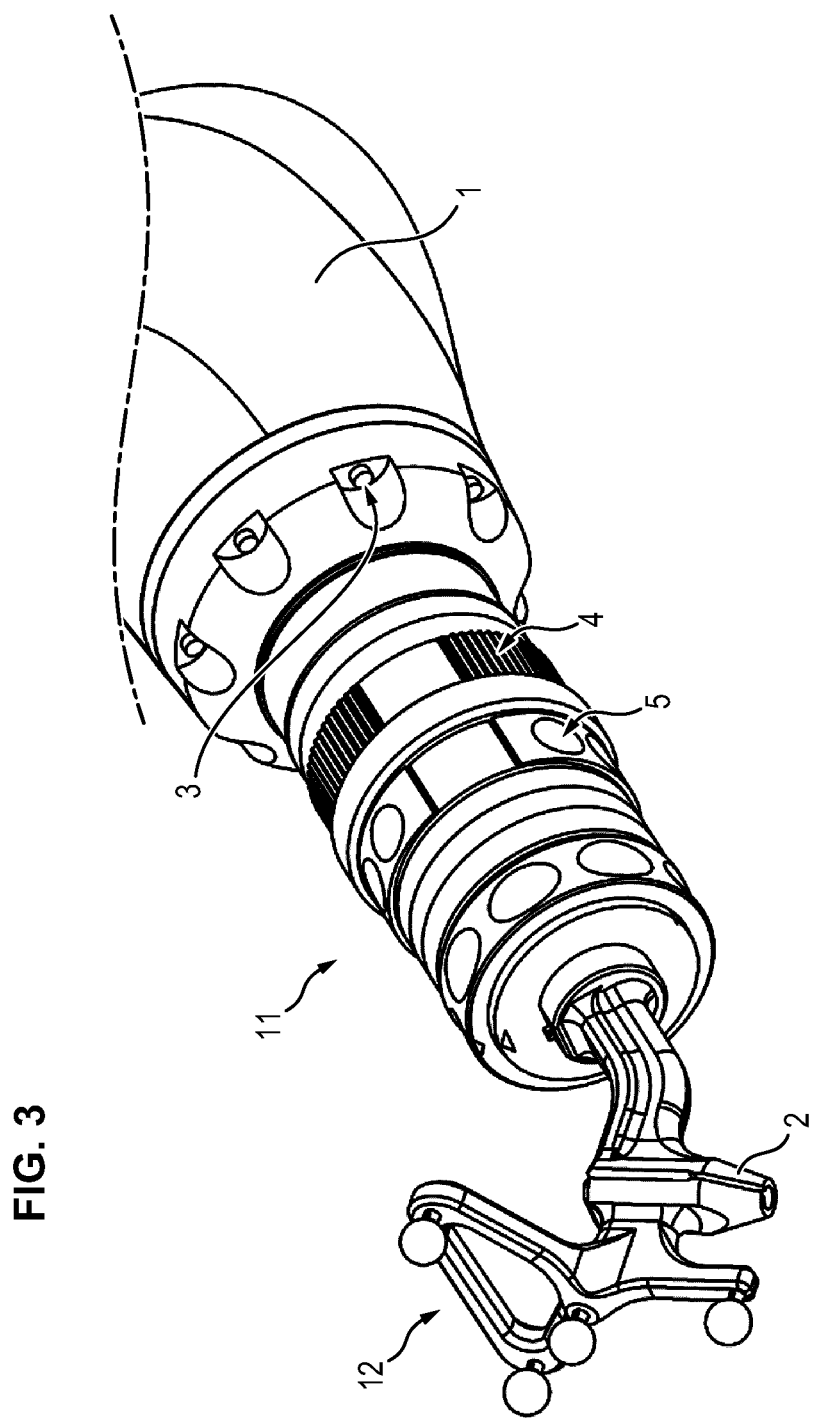
FIG. 3 is a perspective view of the end-effector of the robotic arm of FIG. 2.

An enlarged view of the end-effector is shown in FIG. 3.

FIG. 4 provides an embodiment of a state machine describing the operation of the robotic arm by the control unit. The right part of the figure shows the different states of the LEDs ring forming the user interface.

When the system is switched on, an initialization (init) is carried out.

The first step is the selection of the next target to be achieved. Said selection may be made by the user during the planning step. Otherwise, said selection may be made by a double click on the second switch as described above.

The robotic arm is then in an idle mode, waiting for an input from the user. The LEDs emit a blinking white light.

If the user activates the first switch (Primary input pressed), the robotic arm enters the hand guiding mode, which is maintained as long as the first switch is activated. When the user releases the first switch (Primary input released), the robotic arm returns to the idle mode.

If the user activates the second switch (Secondary input pressed), the robotic arm enters the computed trajectory mode and moves to the selected target. This mode can be activated only if the tracker attached to the end-effector is detectable by the localization system (evt_tracker_visible). The computed trajectory target is maintained as long as the target has not been reached and the second switch is activated. In this state, the LEDs emit a steady white light.

If the user releases the second switch and the target has not been reached yet (Secondary input released), the robotic arm returns to the idle mode.

If the target has been reached (this situation being detected by the control unit comparing the position of the target and the position of the tracker attached to the end-effector), the LEDs emit a steady green light.

The user thus has to release the second switch to enter the servo-controlled (servoing) mode.

During the servo-controlled mode, the control unit continuously monitors whether the tracker attached to the end-effector is in the field of view of the localization system (is_tracker_visible loop). If said tracker becomes undetectable by the localization system (evt_tracker_invisible), the servo-controlled mode is interrupted and the LEDs emit a steady orange light. The robotic arm enters a waiting-for-tracker mode until the tracker becomes detectable again (evt_tracker_visible). The robotic arm thus returns to the servo-controlled mode and the LEDs emit the steady green light again.

If the control unit detects an unmet safety condition, such as a motion of the robotic arm exceeding a predetermined amplitude, direction, acceleration and/or speed in the servo-controlled mode, it activates a safety mode inhibiting movement of the robotic arm (evt_safety_mode_activated) and the robotic arm returns to the idle mode.

REFERENCES

US 2011/0190790
US 2014/0350571
EP2868277
EP3361977

The invention claimed is:

1. A surgical robotic system comprising a robotic arm an end-effector and a control unit configured to controllably move the robotic arm and maintain the end-effector in at least one target position relative to a patient, wherein the control unit is configured to:
   (i) based on a first input continuously applied by a user onto the robotic arm, activate a hand guiding mode wherein the robotic arm is freely movable by the user;
   (ii) based on a second input different from the first input, continuously applied by the user onto the robotic arm, activate a computed trajectory mode wherein the robotic arm moves to a target position according to a computed trajectory;
   (iii) when the computed trajectory mode is activated, detect that the end-effector meets at least one predetermined safety condition and automatically switch to a servo-controlled mode wherein the robotic arm is automatically movable to maintain the end-effector in the target position relative to a tracker attached to the patient.

2. The surgical robotic system of claim 1, wherein the target position is selected from:
   a drilling axis;
   a drilling axis and a drilling depth;
   a cutting plane; and
   an optimal working position of an active surgical tool.

3. The surgical robotic system of claim 1, wherein the predetermined safety condition is that the tracker attached to the patient remains in a controlled volume relative to a base of the robotic arm, a dimension of said controlled volume being greater in a direction of an expected motion of the tracker than in a direction of an unexpected motion of said tracker.

4. The surgical robotic system of claim 1, wherein the control unit is configured to adjust the computed trajectory based on an orientation of the robotic arm imposed by the user in the hand guiding mode.

5. The surgical robotic system of claim 1, further comprising a user interface coupled to the control unit and configured to provide information on the current mode.

6. The surgical robotic system of claim 5, wherein the user interface comprises a display monitor arranged on the robotic arm and configured to display a changing graphical item depending on the current mode.

7. The surgical robotic system of claim 5, wherein the user interface comprises a ring including a plurality of LEDs configured to have predetermined colors and/or blinking conditions depending on the current mode.

8. The surgical robotic system of claim 1, wherein the control unit is further configured to activate a safety mode inhibiting movement of the robotic arm, based on a detection of motion of the robotic arm exceeding at least one of a predetermined amplitude, direction, acceleration and speed in the servo-controlled mode.

9. The surgical robotic system of claim 1, wherein the control unit is configured to successively maintain the end-effector in a plurality of target positions.

10. The surgical robotic system of claim 1, further comprising a first switch configured for application of the first input by the user and a second switch distinct from the first switch configured for application of the second input by the user.

11. The surgical robotic system of claim 10, wherein the control unit is configured to enable a transition between two successive targets when a double-click of the second switch is done by the user at any time during the surgical procedure.

12. The surgical robotic system of claim 1, wherein the control unit is configured to put the robotic arm in idle mode when the tracking of said robotic arm is not enabled and the surgical robotic system is either in hand guiding mode or computed trajectory mode.

13. The surgical robotic system of claim 1, wherein the control unit is configured to put the robotic arm in a specific waiting mode when the tracking of said robotic arm is lost when the surgical robotic system is in the servo-controlled mode, wherein said specific waiting mode can switch back to the servo-controlled mode when the tracking is retrieved.

14. A process for positioning an end-effector held by a robotic arm relative to a patient, comprising:
   (i) based on a first input continuously applied by a user onto the robotic arm, activating a hand guiding mode wherein the robotic arm is freely movable by the user;
   (ii) based on a second input different from the first input, continuously applied by the user onto the robotic arm, activating a computed trajectory mode wherein the robotic arm moves to a target position according to a computed trajectory;
   (iii) when the computed trajectory is activated, detect that the end-effector is within a controlled volume around the target position, and automatically switch to a servo-controlled mode wherein the robotic arm is automatically movable within said controlled volume to maintain the end-effector in the target position relative to the patient.

15. The process of claim 14, wherein the target position is planned relative to the patient's spine.

16. The process of claim 14, wherein the target position is planned relative to a patient's bone.

* * * * *